United States Patent

Herzberg

(12) United States Patent
(10) Patent No.: US 6,569,111 B2
(45) Date of Patent: May 27, 2003

(54) WRIST BANDAGE

(75) Inventor: Thorsten Herzberg, Langenhorner Chaussee (DE)

(73) Assignee: Beiersdorf AG, Hamburg (DE)

( * ) Notice: Subject to any disclaimer, the term of this patent is extended or adjusted under 35 U.S.C. 154(b) by 0 days.

(21) Appl. No.: 09/916,006

(22) Filed: Jul. 26, 2001

(65) Prior Publication Data

US 2002/0040201 A1 Apr. 4, 2002

(30) Foreign Application Priority Data

Jul. 29, 2000 (DE) .......................... 100 37 341

(51) Int. Cl.⁷ ................................ A61F 13/00
(52) U.S. Cl. ............................. 602/64; 602/21; 602/22; 602/75
(58) Field of Search .................. 602/1, 5, 6, 20–22, 602/60–62, 64, 75; 601/1, 5

(56) References Cited

U.S. PATENT DOCUMENTS

| | | | | |
|---|---|---|---|---|
| 3,238,939 A | * | 3/1966 | Stubbs | |
| 3,512,776 A | * | 5/1970 | Thomas | |
| 4,665,909 A | * | 5/1987 | Trainor | |
| 4,787,381 A | * | 11/1988 | Hubbard et al. | |
| 4,836,195 A | * | 6/1989 | Berrehail | |
| 5,036,838 A | * | 8/1991 | Sherman | |
| 5,350,418 A | * | 9/1994 | Janevski et al. | |
| 5,397,296 A | * | 3/1995 | Sydor et al. | |
| 5,459,883 A | * | 10/1995 | Garceau-Verbeck | |
| 5,592,694 A | * | 1/1997 | Yewer | |
| 5,819,313 A | * | 10/1998 | McCrane | |
| 5,928,172 A | * | 7/1999 | Gaylord | |
| 5,971,945 A | * | 10/1999 | Garris | |
| 6,120,470 A | * | 9/2000 | Bodenschatz et al. | |
| 6,315,748 B1 | * | 11/2001 | Morgan, Jr. | |

\* cited by examiner

*Primary Examiner*—Nicholas D. Lucchesi
*Assistant Examiner*—Lalita M Hamilton
(74) *Attorney, Agent, or Firm*—Norris McLaughlin & Marcus

(57) ABSTRACT

Wrist bandage 1 with a first angled strip 10 which consists of two branches 101, 102 which run together at an acute angle and whose inner edges 131, 132 are connected to one another at least in sections, and with a second elongate strip 40 which is attached to the second branch 102 of the angled strip 10. In the transition area between the branches 101, 102, a substantially round incision 30 is made which starts in the first branch 101 and extends into the second branch 102 and, when the bandage 1 is applied, serves to receive the thumb, and which, in the distal forearm area, at the transition to the carpal area, wraps round the carpal area in a circle.

15 Claims, 5 Drawing Sheets

WRIST BANDAGE

Figure 1:
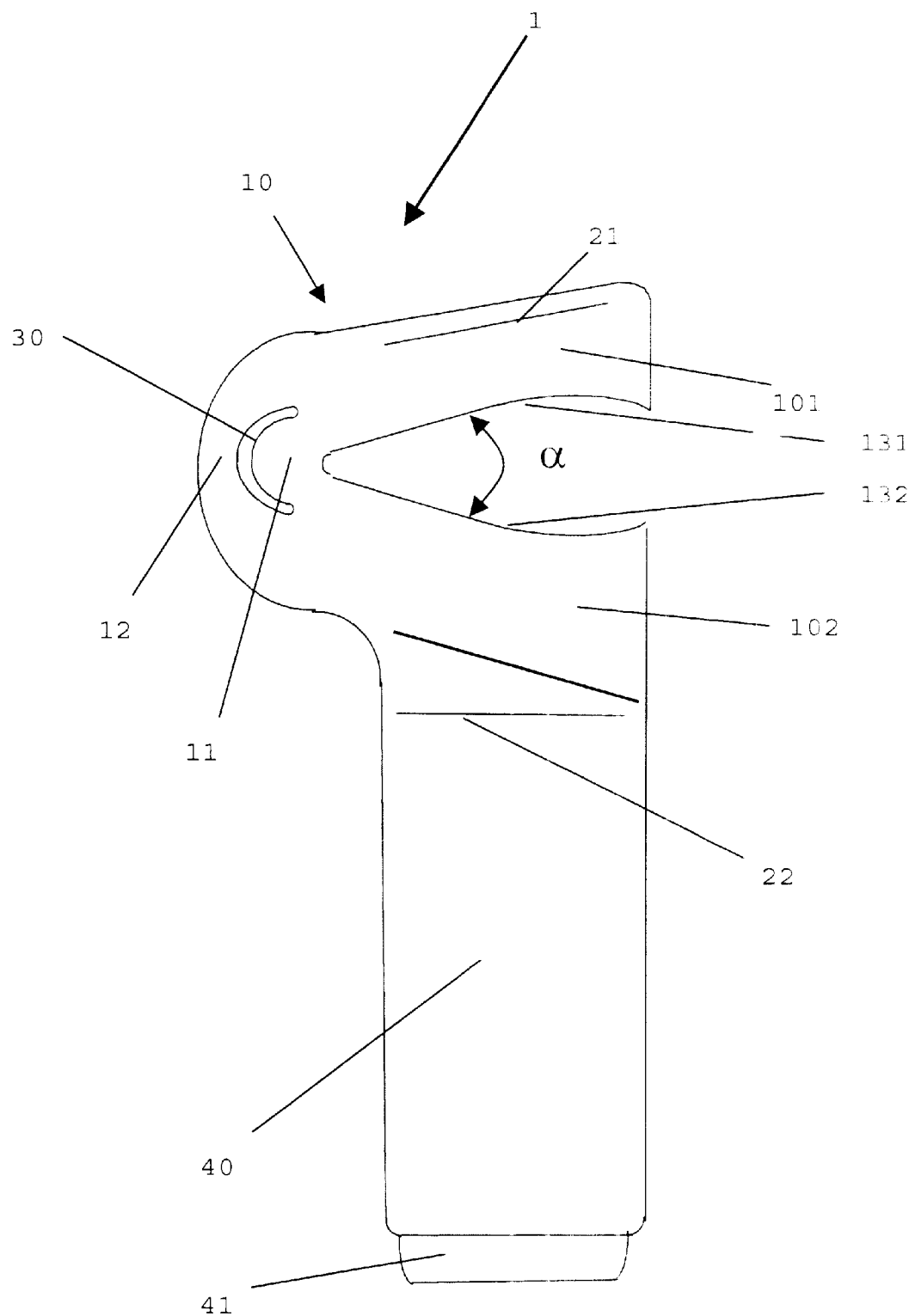

The invention relates to a wrist bandage for injuries to the wrist, for example distortions, mild sprains, extension injuries and structural loosening in the carpal area and in the transitional area to metacarpals 1 to 5, and incipient degenerative changes of the carpo-metacarpal joint of the thumb.

Depending on their design and on the indications for which they are intended, orthopedic bandages exert a fixing, guiding, bracing and/or supporting action on the extremities of the human body.

These medical bandages must have a shape which corresponds to the anatomical circumstances in order to be able to act externally on the human body with a form fit and a force fit.

Medical bandages of this kind are produced by cutting out blanks from planar material, for example neoprene, knitted fabrics or woven fabrics. The anatomically appropriate shape is obtained via the shape of the blanks or darts, for example with gussets, and subsequent joining together of the blanks, as is also customary in articles of clothing.

The joining together can be done by sewing, gluing or other conventional methods.

The great disadvantage of these bandages is that the exact anatomical fit can be achieved only with difficulty and there are a large number of connection points, for example seams. These connection points change the properties of the material used, and there is the danger of pressure points on the skin.

Dressings or bandages for the wrist are used in the treatment of distortions, contusions or sprains of the ulnar and radial ligaments. However, they can also support the healing process in the case of fissures of the metacarpal bones. Finally, by means of appropriate immobilization of the wrist, irritation of the metacarpal joints can be reduced to such a point that it entirely disappears.

EP 0 775 476 A discloses a wrist bandage designed for both hands, using a flexible support material which has been anatomically appropriately shaped and on which two pockets are sewn, in each case in the lateral edge area, and these are used for receiving a splint. The bandage is applied and fixed around the wrist with the aid of several straps.

It is an object of the invention to design a bandage which has a high degree of functionality with proprioceptive action, but which at the same time is easy and uncomplicated for the patient to apply and which, by means of dispensing with rigid elements, offers a high degree of dynamics. Moreover, the bandage should be inexpensive to produce.

This object is achieved by the bandage defined according to the main claim. The subclaims relate to advantageous developments of the bandage.

Accordingly, the invention describes a wrist bandage with a first angled strip which consists of two branches which run together at an acute angle and whose inner edges are connected to one another, in particularly sewn to one another, at least in sections, but preferably along the entire length of the edges, and with a second elongate strip which is attached to the second branch of the angled strip and which, in the distal forearm area, at the transition to the carpal area, wraps round the carpal area in a circle.

In the transition area between the two branches, a substantially round incision is made which starts in the first branch and extends into the second branch and, when the bandage is applied, serves to receive the thumb.

In a first advantageous embodiment of the bandage, the angle α between the branches of the angled strip is between 20° and 45°, in particular between 25° and 40°.

In a further advantageous embodiment of the bandage, a connection strip is provided which is attached at one end to the elongate strip and is attached at the other end to the first branch of the angled strip.

In the distal forearm area, at the transition to the carpal area, the elongate strip of the bandage wraps round the carpal area in a circle, and preferably in such a way that it can be closed. In addition, the thumb is provided in a kind of loop with a tongue-like support.

From the thumb to the carpal area, the blank of the bandage is connected by a seam. This seam, by virtue of its design, ensures an excellent anatomical fit and support of the thumb of the bandage in the thumb/carpal area.

Moreover, the preferred integration of a connection piece, a preferably elastic textile part, on the inside of the bandage, ensures that the bandage is easy to apply and secure in position in the open state using just one hand.

From the aspect of biomechanics, it has proven particularly advantageous if, in the bandage, the cutout for the thumb is in a U-shape and has a certain height-to-width ratio, since only in this way is it possible to provide a support for the thumb and a thumb loop. The height H of the thumb loop in relation to the width B preferably has a ratio of 1 to 1.0 through 2.2, particularly preferably 1 to 1.7.

In a further preferred embodiment, the bandage is made of a material which is laminated at least on both sides and which has a velcro-like velour on the outside, or has partially attached velcro areas on the outside, and a skin-compatible textile material on the inside.

Moreover, spacer fabrics with corresponding laminations can be used or, in the case of technical machine finishing, also without laminations.

Such spacer fabrics are disclosed in EP 0 071 212 B1. Spacer fabrics are mat-like laminated articles with a top layer of woven fiber or filament, a bottom layer, and, between these layers, individual or clustered holding fibers which, distributed across the surface of the laminated article, are needled through the particle layer and join the top layer and the bottom layer together. In an additional feature according to EP 0 071 212 B1, but not an essential one, particles of inert stone, for example sand, gravel or the like, are provided in the holding fibers.

The holding fibers needled through the particle layer maintain the top layer and the bottom layer at a distance from each other and they are connected to the top layer and the bottom layer.

Woven or knitted spacer materials are described inter alia in two articles, namely:

an article from the specialist journal "kettenwirk-praxis 3/93", 1993, pages 59 to 63 "Raschelgewirkte Abstandsgewirke" [Raschel-knit spacers] and an article from the specialist journal "kettenwirk-praxis 1/94", 1994, pages 73 to 76 "Raschelgewirkte Abstandsgewirke" [Raschel-knit spacers]

and reference is hereby made to their content, and their content is part of this disclosure and invention.

Preferred materials are neoprene foam, polyurethane foam or polyester foam, and these are preferably perforated for better aeration.

In a further preferred embodiment of the bandage, the material has an elasticity of 30 to 150% in the X axis and of 5 to 70% in the Y axis, where the X axis runs in a circle round the forearm and wrist in the applied state of the bandage, and the Y axis, again in the applied state of the bandage, runs along the length of the forearm, i.e. longitudinally.

In a further preferred embodiment of the bandage, the material for the connection part has an elasticity of 50 to 200% in the X axis and of 0 to 50% in the Y axis, where the X axis runs in a circle round the forearm and wrist in the applied state of the bandage, and the Y axis, again in the applied state of the bandage, runs along the length of the forearm, i.e. longitudinally.

Finally, an excellent configuration of the bandage is obtained if the forearm part and the elongate strip have one or more velcro closures or press studs.

Thus, the bandage according to the invention differs markedly from conventional bandages which in general only enclose the wrist or in some cases also just the distal end of the ulna and radius.

The bandage places hardly any restriction on the physiological range of movement of the hand and in addition to an adaptive grip also permits a plunging grip. The circular compression of the bandage in the carpal area provides a feeling of increased joint strength. By this means, movements which would otherwise be painful are once again possible, which results in improved overall circulation and nutrition of the capsular ligament apparatus.

The invention is explained in more detail with reference to six diagrammatic drawings of an illustrative embodiment, without this implying any unnecessary limitation on the invention.

Figure 2:
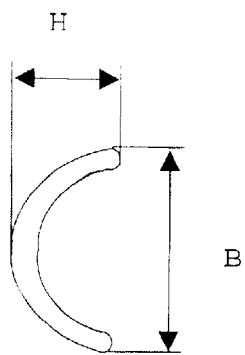
Figure 3:
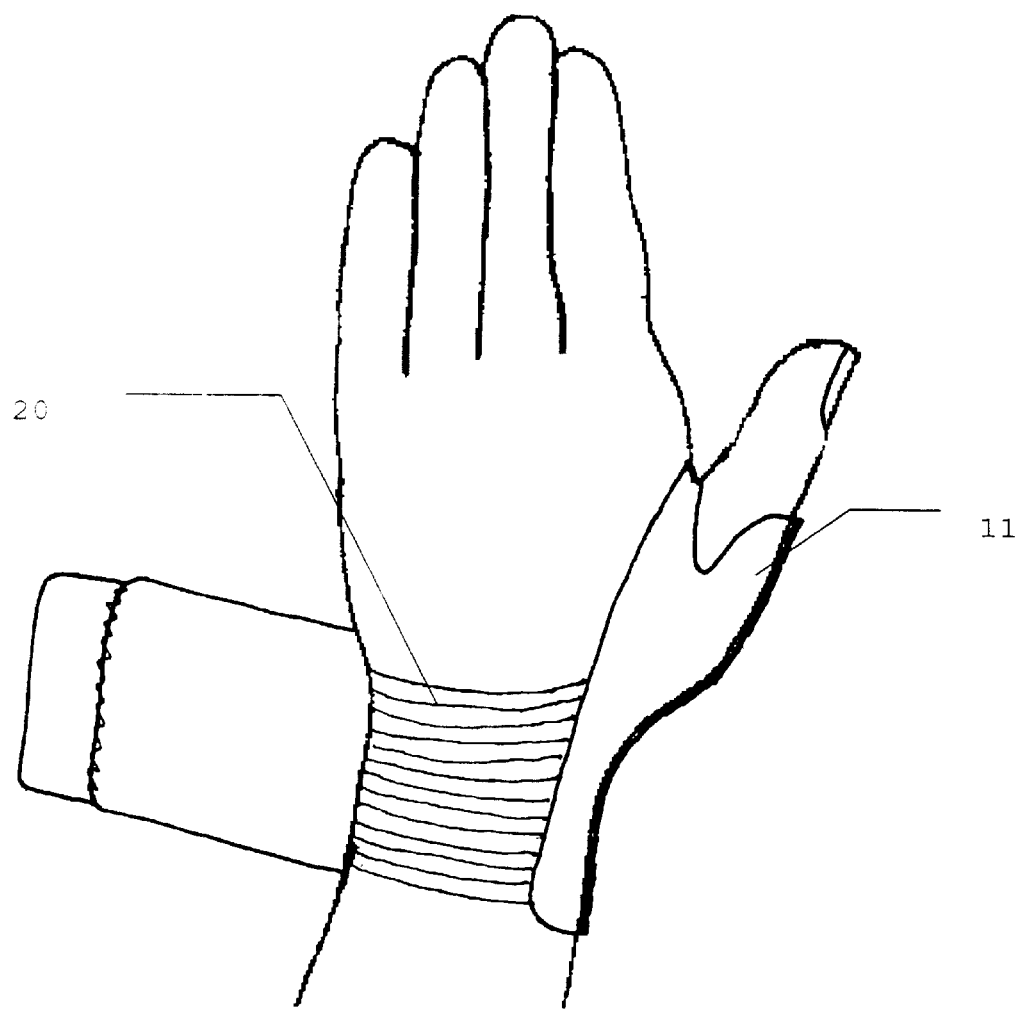
Figure 4:
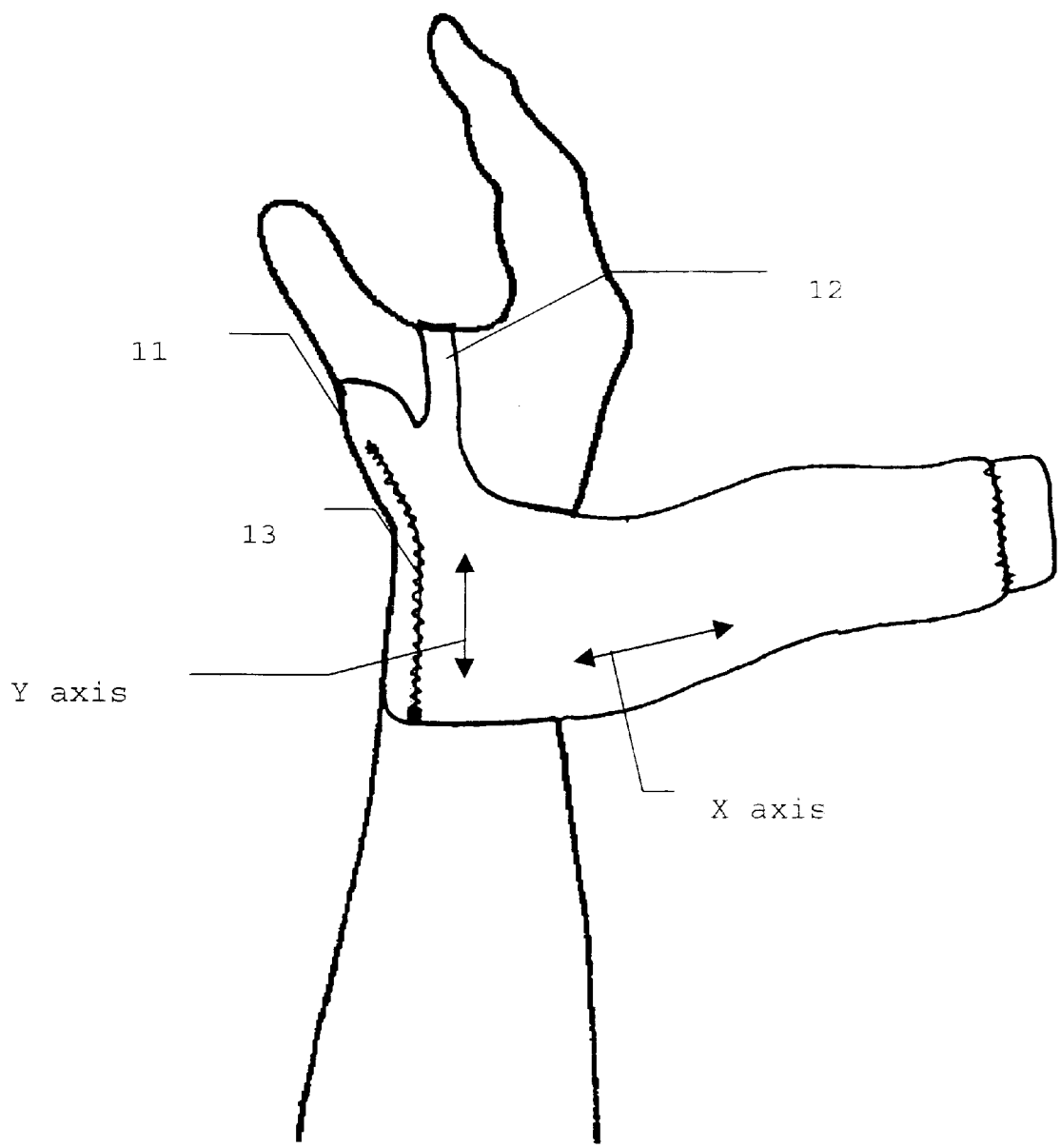
Figure 5:
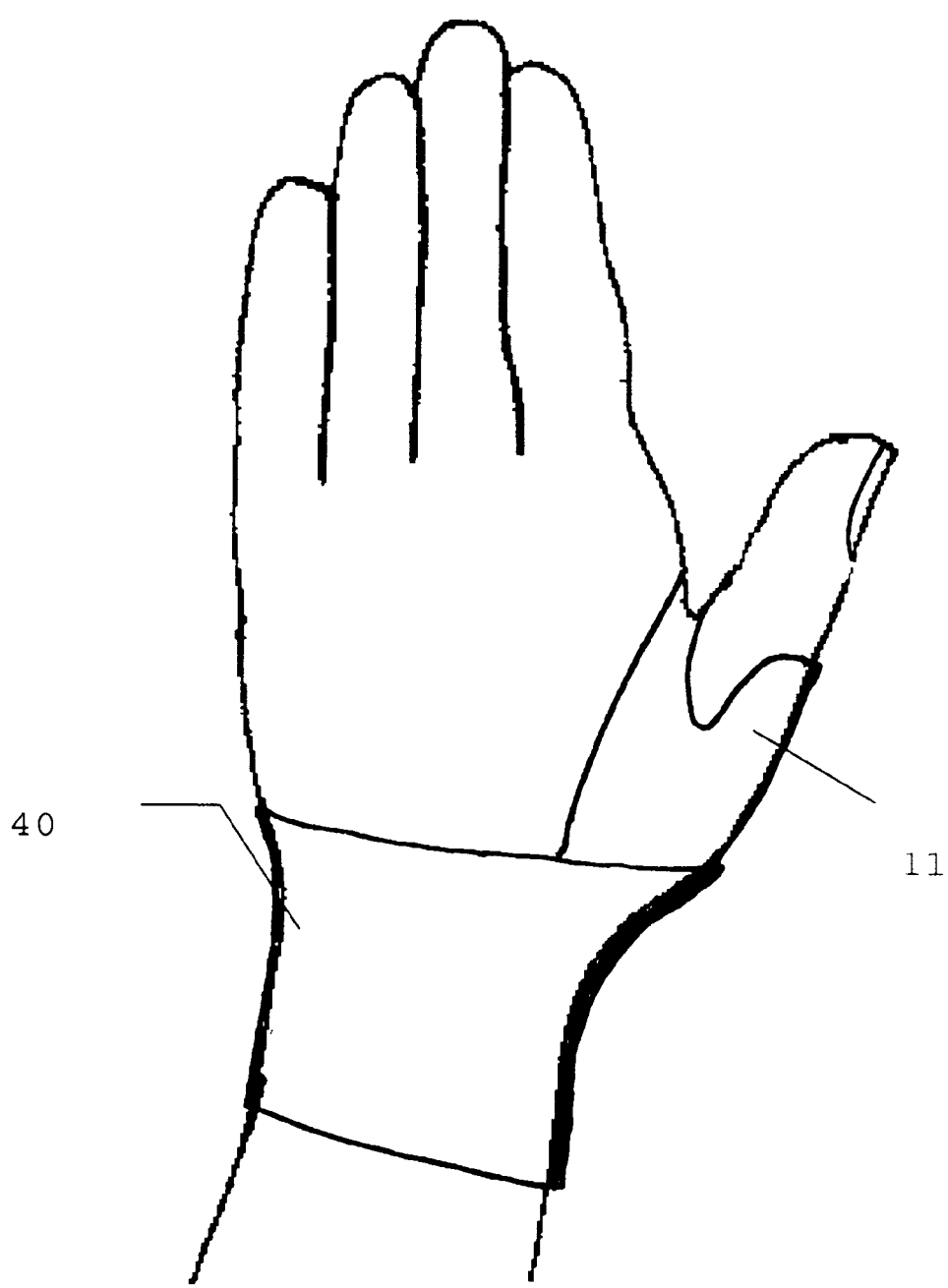
Figure 6:
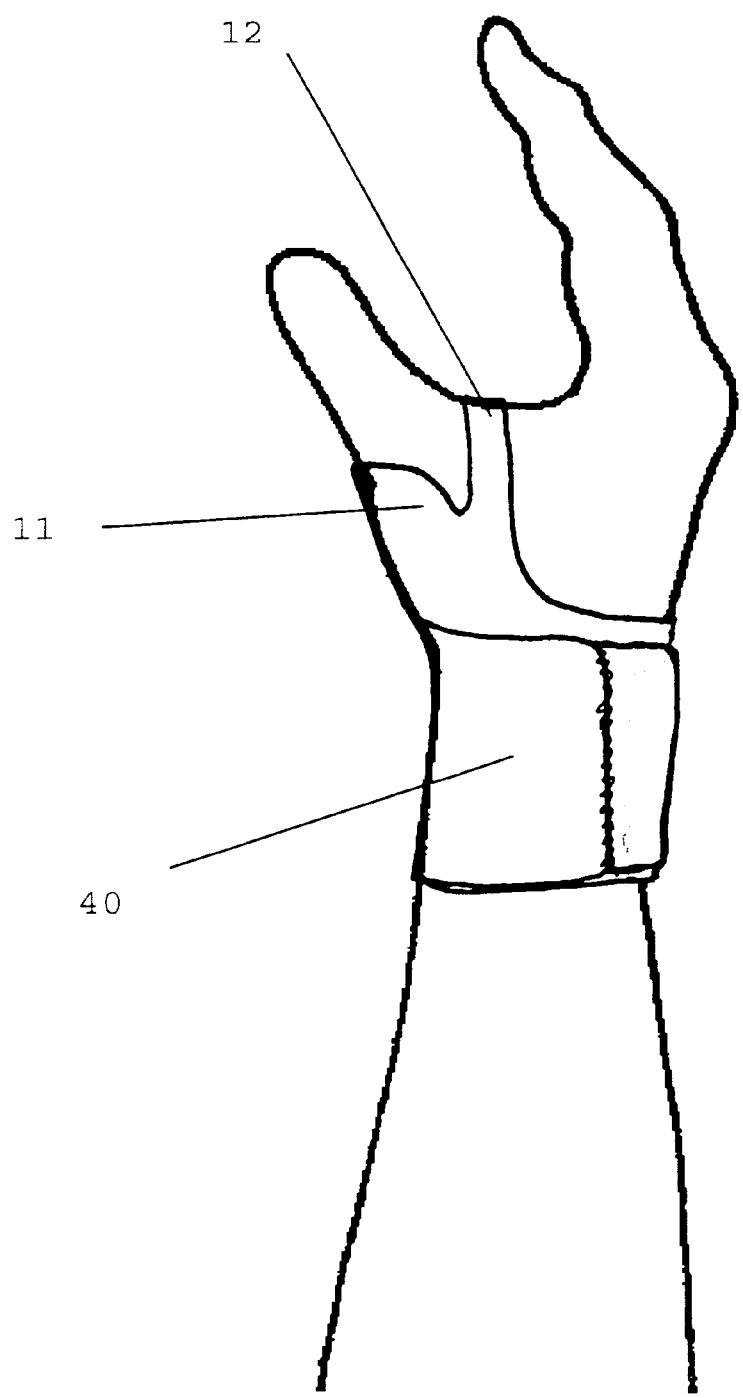

In the drawings:

FIG. 1 shows the blank for a particularly advantageous embodiment of the bandage, FIG. 2 shows details of the incision in the bandage which, when the bandage is applied, serves to receive the thumb, FIG. 3 shows the bandage half applied, in a dorsal view, FIG. 4 shows the bandage half applied, in a medial view, FIG. 5 shows the applied bandage in a dorsal view, and FIG. 6 shows the applied bandage in a medial view.

In FIG. 1, the blank for a wrist bandage according to the invention is shown. The bandage is made up of a first angled strip 10 which for its part is made up of two branches 101, 102 which run together at an acute angle, and a second elongate strip 40 which is attached to the second branch 102 of the angled strip 10.

In the transition area between the branches 101, 102, a substantially round incision 30 starts in the first branch 101 and extends into the second branch 102 and, when the bandage 1 is applied, serves to receive the thumb.

Thus, the transition area between the branches 101, 102 forms a thumb loop 12, which wraps round the thumb at the root, and it also forms a thumb support 11 which limits the movement of the thumb and at the same time offers support for the thumb.

In the distal forearm area, at the transition to the carpal area, the second strip 40 wraps round the carpal area in a circle. Provided at the end of the second strip 40 there is a tongue 41 which adheres to the strip 40 itself, particularly by means of a velcro arrangement, so as to fix the strip 40.

Between the branches 101, 102 of the angled strip 10, the bandage 1 has in particular an angle α of between 20° and 45°, in the present case an angle of 35° is present.

To produce the bandage 1, the inner edges 131, 132 of the two branches 101, 102 are connected to one another at least in sections, but preferably the entire length of the edges 131, 132. This is preferably done by stitching. The seam 13 starts from the transverse edges of the branches 101, 102 lying opposite the transition area, and extends as far as the transition area itself.

In the advantageous embodiment of the bandage 1 shown here, a connection strip 20 is provided which is attached at one end to the elongate strip 40 and is attached at the other end to the first branch 101 of the angled strip 10. The connection strip is preferably also secured by stitching at the seams 21, 22 shown.

FIG. 2 shows details of the incision 30 in the bandage 1, which incision 30 serves to receive the thumb when the bandage 1 is applied.

The cutout 30 is preferably U-shaped, and with a defined height-to-width ratio. This guarantees a support for the thumb and ensures that a thumb loop can be formed. The height H of the thumb loop in relation to the width B is preferably in a ratio of 1 to 1.0 through 2.2, particularly preferably 1 to 1.7.

FIGS. 3 and 4 show the half-applied bandage in a dorsal view and in a medial view, respectively.

The two branches 101, 102 of the angled strip 10 are connected to each other by the seam 13, and in particular in such a way that the thumb support 11 and the thumb loop 12 are formed.

By virtue of the preferred integration of the connection piece 20, which is advantageously an elastic textile part, the bandage 1 is easy to apply and securely position in the open state using just one hand.

The material of the bandage has an elasticity of 30 to 150% in the X axis and of 5 to 70% in the Y axis, where the X axis runs in a circle round the forearm and wrist in the applied state of the bandage, and the Y axis, again in the applied state of the bandage, runs along the length of the forearm, i.e. longitudinally (see FIG. 4).

Finally, FIGS. 5 and 6 show the applied bandage 1 viewed from the dorsal and medial directions.

The second strip 40 wraps round the carpal area in a circle. The strip 40 is fixed to same strip 40 by means of a preferred velcro arrangement on the tongue 41.

What is claimed is:

1. A wrist bandage having a flexible and elastic connection strip for additional support, the bandage further comprising a first angled strip which consists of two branches which run together at an acute angle and whose inner edges are connected to one another;

a second elongate strip adapted for wrapping around the carpal area, wherein the second elongate strip is attached to the second branch of the angled strip wherein the transition area between the branches comprises a substantially round incision which starts in the first branch and extends into the second branch, the round incision adapted for receiving and supporting a thumb, and the connection strip comprising two ends each of which is secured to the bandage, wherein between said ends extends a non-secured elastic strip that supports the wrist between the connection strip and bandage prior to completing application of the bandage.

2. The bandage as claimed in claim 1, wherein the angle α between the branches of the angled strip is between 20° and 45°.

3. The bandage as claimed in claim 1, wherein the height H of the thumb loop in relation to the width B has a ratio of 1 to 1.0 through 2.2.

4. The bandage as claimed in claim 1, wherein a connection strip is provided which is attached at one end to the elongate strip and is attached at the other end to the first branch of the angled strip.

5. The bandage as claimed in claim 1, wherein the bandage is made of a material chosen from the group consisting of a material which is laminated at least on both sides and has velour on the outside and skin-compatible textile fabric on the inside, or alternatively, the bandage is made of a spacer fabric.

6. The bandage as claimed in claim 5, wherein the materials used are neoprene foam, polyurethane foam or polyester foam, which are optionally perforated.

7. The bandage as claimed in claim 1, wherein the elongate strip has one or more closure mechanisms selected from the group consisting of hoop and loop closures and press studs.

8. The bandage of claim 1, wherein the bandage material has an elasticity of less than 150%.

9. The bandage of claim 1, wherein the bandage material has an elasticity of up to 70% in the direction of the Y-axis.

10. The bandage of claim 1, wherein the bandage material has an elasticity of between 30 to 200% in the direction of the X-axis.

11. The bandage of claim 1, wherein the inner edges of the branches are connected to each other along their entire lengths.

12. The bandage of claim 1, wherein the inner edges of the branches are connected to each other for a distance that is less than their entire lengths.

13. The bandage of claim 1, wherein the first angled strip is adapted to support the root of a thumb when the thumb is inserted through the substantially round incision.

14. The bandage of claim 1 wherein the elongate strip and the branches are made of flexible and elastic material.

15. The bandage of claim 1 wherein the connection strip is secured at one end to the elongate strip, and at the other end to a branch of the angled strip.

* * * * *